United States Patent
Safai et al.

(10) Patent No.: US 7,568,832 B2
(45) Date of Patent: Aug. 4, 2009

(54) IMAGING METHOD TO VERIFY ELECTRICAL CONDUCTIVITY ACROSS LIGHTNING STRIKE PROTECTION BOUNDARIES

(75) Inventors: Morteza Safai, Seattle, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 205 days.

(21) Appl. No.: 11/383,018

(22) Filed: May 12, 2006

(65) Prior Publication Data

US 2009/0129431 A1    May 21, 2009

(51) Int. Cl.
    *G01N 25/72* (2006.01)
(52) U.S. Cl. .......................................... 374/10; 374/11
(58) Field of Classification Search .................. 374/5, 374/10, 11, 57, 121; 324/240, 238, 525
    See application file for complete search history.

(56) References Cited

U.S. PATENT DOCUMENTS

| | | | | |
|---|---|---|---|---|
| 4,747,310 A | * | 5/1988 | Collins et al. ................... 73/661 |
| 4,760,493 A | * | 7/1988 | Pearson ....................... 361/218 |
| 5,397,530 A | * | 3/1995 | Narasimhan et al. ........... 419/1 |
| 5,417,494 A | * | 5/1995 | Kempa et al. .................. 374/5 |
| 6,106,463 A | * | 8/2000 | Wilk .......................... 600/437 |
| 6,492,630 B2 | * | 12/2002 | Nagahira ..................... 219/619 |
| 6,636,037 B1 | * | 10/2003 | Ou-Yang .................... 324/240 |
| 7,287,902 B2 | * | 10/2007 | Safai et al. ..................... 374/5 |
| 7,307,431 B2 | * | 12/2007 | Safai et al. .................. 324/639 |
| 7,312,608 B2 | * | 12/2007 | Georgeson et al. .......... 324/240 |
| 7,333,898 B2 | * | 2/2008 | Griess et al. .................. 702/35 |
| 2006/0274812 A1 | * | 12/2006 | Safai et al. ..................... 374/5 |
| 2007/0017297 A1 | * | 1/2007 | Georgeson et al. ............ 73/801 |
| 2007/0095160 A1 | * | 5/2007 | Georgeson et al. ............ 73/866 |
| 2007/0096751 A1 | * | 5/2007 | Georgeson et al. .......... 324/691 |
| 2007/0100582 A1 | * | 5/2007 | Griess et al. ................ 702/183 |
| 2007/0125189 A1 | * | 6/2007 | Bossi et al. ................ 73/865.8 |
| 2008/0000299 A1 | * | 1/2008 | Georgeson ................... 73/606 |
| 2008/0061774 A1 | * | 3/2008 | Georgeson et al. .......... 324/240 |

* cited by examiner

*Primary Examiner*—Harshad Patel
*Assistant Examiner*—Freddie Kirkland, III
(74) *Attorney, Agent, or Firm*—Felix L. Fischer

(57) ABSTRACT

A rapid image-based method for validating good electrical contact between existing LSP material on a structure, and LSP material on an applied patch, thus ensuring continuous LSP through the patch. The method and apparatus are used in the repair of LSP by validating an electrical connection between new and existing LSP materials. It can also be used during manufacturing to ensure good contact between sections of LSP material.

6 Claims, 4 Drawing Sheets

IMAGING METHOD TO VERIFY ELECTRICAL CONDUCTIVITY ACROSS LIGHTNING STRIKE PROTECTION BOUNDARIES

BACKGROUND OF THE INVENTION

1. Field of the Invention

The present invention relates to lightning strike protection (LSP) in composite structures. More particularly, the invention provides a method and system for examining a repair to a composite structure with LSP by imaging for detecting thermal gradients in an inductively heated LSP mesh at the periphery of the repair.

2. Description of the Related Art

Aircraft are being designed and built with greater percentages of composite material. For example, the Boeing 787 currently under development by the assignee of the present invention will have more than 50% composites for its primary structure. Although composites are lighter and have better mechanical and fatigue properties than traditional aluminum, they are less electrically conductive, and have limited electromagnetic shielding, causing reduced current dissipation at the lightning strike attach point. Compared to traditional aluminum, composites are therefore subject to greater damage due to lightning strikes.

When lightning hits an aircraft, a direct, conductive path on the skin of the aircraft will allow the electricity to travel along the skin, and exit at some other location. Without an adequate conductive path, arcing and hot spots can occur that will char, delaminate, or penetrate the skin, reducing the load-bearing characteristics of the structure. Also, the low shielding capability of composite materials increases the likelihood that electrical circuits will be affected by the lightning strike. One way to protect composite skins from lightning strike damage is to include conductive lightning strike protection (LSP) either in or on the composite skins of an aircraft. For composite components that experience a lot of lightning strikes, such as radomes, rudder tips, elevator tips and aileron tips, LSP often consists of aluminum frames or strips bonded/fastened to the structure and electrically bonded to it. For larger areas, this LSP method is not practical or cost effective. Other methods, such as expanded aluminum foil bonded to the surface, aluminum flame spray coatings, or aluminum coated glass fabric used as a surface layer can all be used for LSP. An approach being developed for 787 is a copper mesh or grid embedded into the skin or backed by film adhesive that is bonded to the skin surface.

A problem arises when a composite skin containing lightning strike protection is damaged and has to be repaired. After the damage is cut away, a composite patch (either pre-cured or cured in-place) is used to replace the material. Even if the patch contains LSP, it is critical to ensure a good conductive path between the patch and surrounding material. Recent test have demonstrated that the patch will be damaged or destroyed if lightning current cannot pass through it. The problem of applying patches that do not reduce, but rather extend the useful LSP area is a significant one.

Until recently, only direct electrical conductivity measurements to verify good contact between the LSP on the structure and the applied patch were available. Measurements were taken all around the patch edge. These were tedious, and did not have high efficacy. The same issue arises for boundaries between individual sections of LSP material during manufacturing.

A recent invention disclosed in U.S. patent application Ser. No. 11/266,052 filed on Nov. 3, 2005 entitled SYSTEMS AND METHODS FOR INSPECTING ELECTRICAL CONDUCTIVITY IN COMPOSITE MATERIALS having a common assignee with the present application is one approach for addressing this problem.

SUMMARY OF THE INVENTION

This present invention is a rapid image-based method for validating there is a good electrical contact between existing LSP material on a structure, and LSP material on an applied patch, thus ensuring continuous LSP through the patch. The inventive method and system are used in the repair of LSP by validating an electrical connection between new and existing LSP materials and also used during manufacturing to ensure good contact between sections of LSP material.

The inventive method for verifying electrical conductivity across boundaries of lightning strike protection (LSP) material employs generating eddy currents in LSP material proximate a joining boundary in the material which generates heat in the LSP material due to the generated eddy currents. A thermal image of the heated LSP material is obtained and the boundary connectivity and resistivity is categorized wherein a well-bonded LSP material boundary will have a uniform thermal image, while thermal "peaks" demonstrate high resistance and thermal "plateaus" demonstrate low resistance, with thermal valleys demonstrating complete breaks/no conduction.

The thermal imaging is accomplished in various embodiments using differential thermal imaging wherein an initial image of the repaired surface being measured is taken prior to induction heating. This data is then subtracted from the subsequent image.

BRIEF DESCRIPTION OF THE DRAWINGS

These and other features and advantages of the present invention will be better understood by reference to the following detailed description when considered in connection with the accompanying drawings wherein.

DETAILED DESCRIPTION OF THE INVENTION

Figure 1:
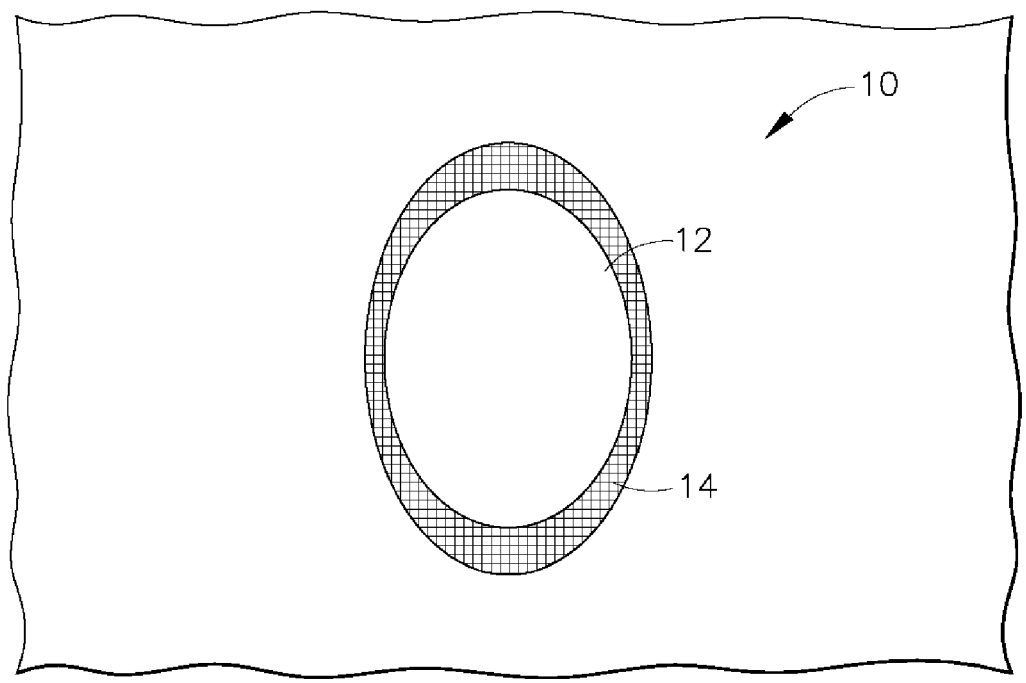
FIG. 1 is a front view of a patch in a composite skin structure with LSP mesh at the periphery of the patch exposed.
Figure 2:
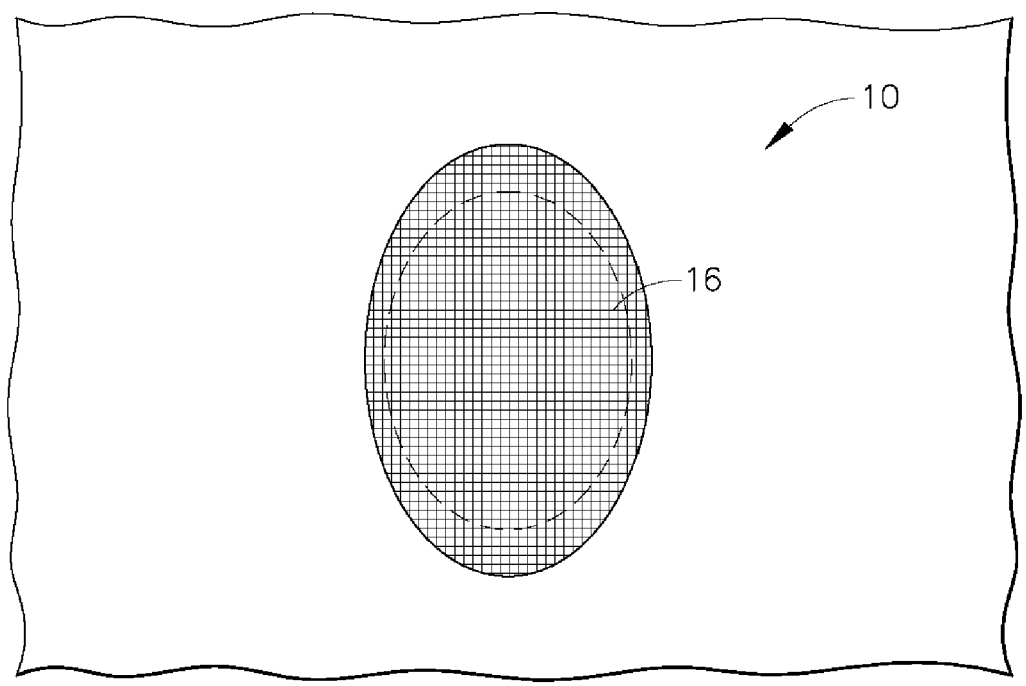
FIG. 2 is a front view of the patched composite skin with LSP mesh applied over the patch and exposed peripheral LSP material.

The method of the present invention provides an assurance of good contact between two sections of LSP material, such as the copper mesh described previously, which is critical during in-service damage repair. In most cases, the LSP will be external to the skin, bonded onto it, or applied in the form of a decal. During repair of a composite skin the damaged composite area is cut away, along with the LSP in the damaged area, and a patch is applied. Once the patch is applied and cured (or the adhesive between the patch and structure is cured), the edge of the existing LSP mesh surrounding the patch is sanded or etched to reveal the copper (or other conductive media). FIG. 1 shows a composite skin 10 in which a patch 12 has been inserted. Exposed LSP mesh 14 surrounds the patch. As shown in FIG. 2, an LSP patch 16 having a peripheral dimension extending over the circumference of the exposed LSP mesh is then bonded onto the patch using the typical method for that type of LSP material. The LSP applied to the patch in alternative embodiments as a decal with integral pressure sensitive adhesive, or secondarily bonded using heat and pressure with a vacuum bag and hot bonder.

Figure 3:
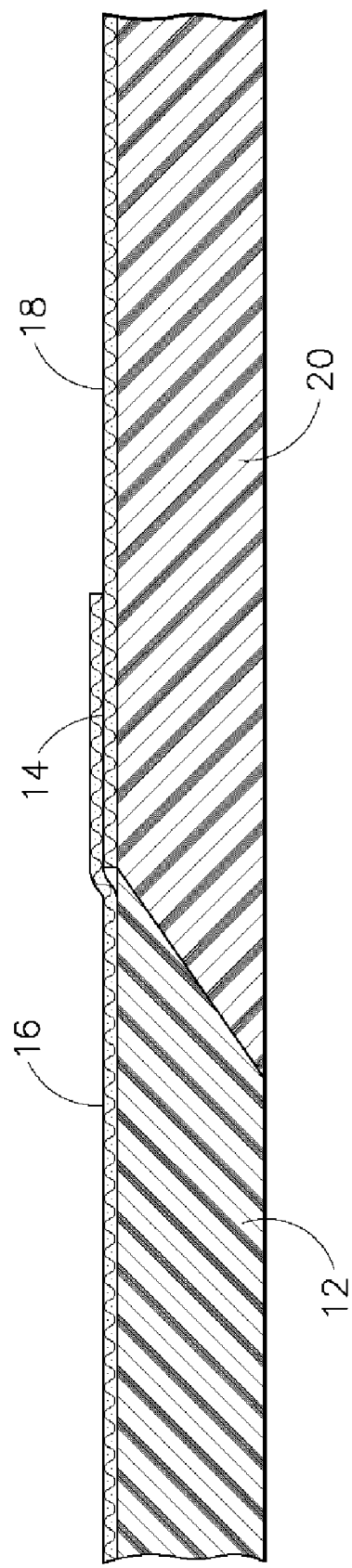
FIG. 3 is a sectional view of the composite skin with the patch in place and the LSP mesh applied to show the LSP layer overlap.

The LSP mesh patch 16 covering the composite patch 12 overlaps the treated area 14 of LSP mesh 18 in the undamaged composite skin 20 at the edge of the patch as shown in FIG. 3 which provides a section view of the edge of the patch and associated LSP. The overlap section of the LSP is exaggerated for clarity. The overlap of LSP produces a region around the patch where the electrical contact needs to be assured for continuity of the LSP.

It is important to ensure that a good electrical connection between the LSP on the patch and main structure all the way around the patch has been achieved. To do this the local electrical pathways need to be checked in some way. Direct electrical conductivity measurements (2 point or 4 point probe) tend to be inconsistent and tedious. The method described in prior filed U.S. patent application Ser. No. 11/266,052 filed on Nov. 3, 2005 entitled SYSTEMS AND METHODS FOR INSPECTING ELECTRICAL CONDUCTIVITY IN COMPOSITE MATERIALS, the disclosure of which is incorporated herein by reference, provides a method for conductivity testing.

Figure 4:
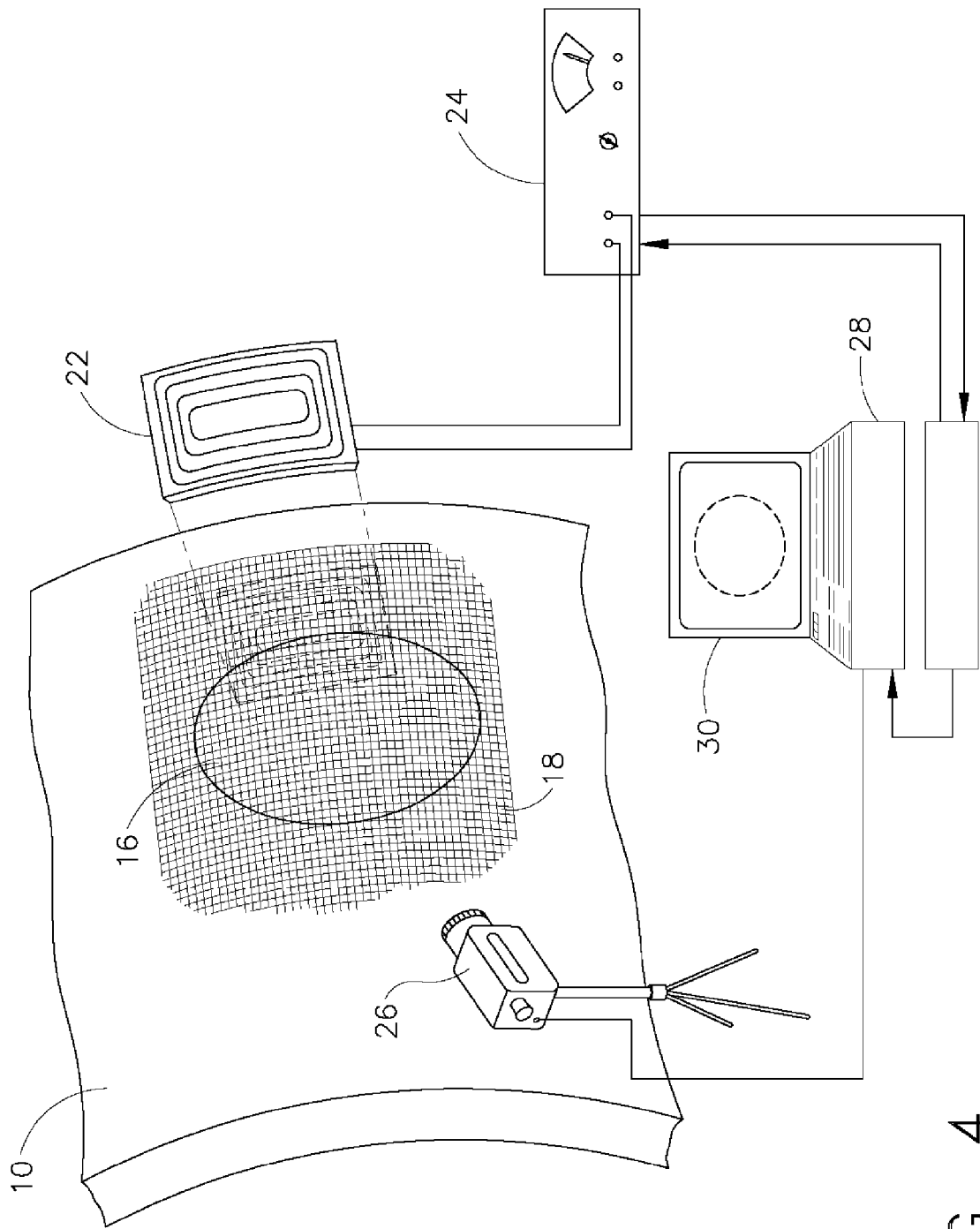
FIG. 4 is a block diagram of the elements of a system for embodying the method of the invention; and, FIG. 5 is a flow chart of the procedural steps of the method of the invention.

The method of the present invention employs a system as shown in FIG. 4. A high power induction coil 22 is provided with a controllable power supply 24. Placing the powered coil in proximity to the composite skin surface 20 induces current flow in the LSP mesh and associated local heating of the mesh. A thermal imaging camera 26 directed at the skin surface with a view field encompassing all or part of the patched area allows recording of the thermal gradient of the heated mesh. A computer data acquisition and control system 28 records the data from the camera and provides control of the power supply for various thermal imaging techniques as will be described in greater detail subsequently.

In instances where the measurement process is conducted in an environment where infrared sources such as overhead lighting may interfere with measurement fidelity, a shade structure or other shield surrounding the fuselage or other surface containing the LSP boundary being measures is erected to avoid extraneous infrared reflection from the boundary.

Figure 5:
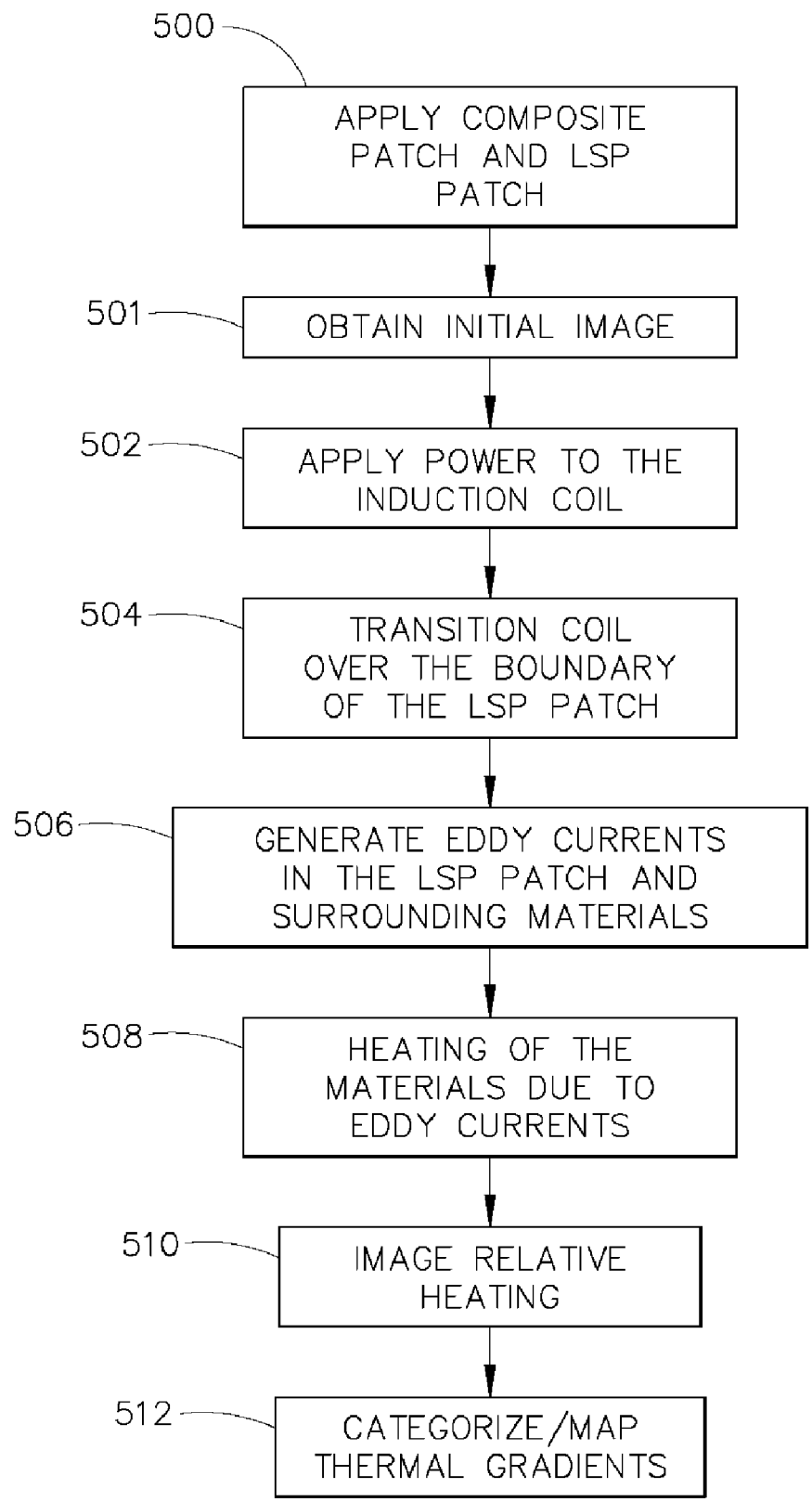

The method of the present invention is shown in the flowchart provided in FIG. 5. The composite patch and LSP patch are applied as previously described, step 500. For certain embodiments with differential imaging processes, an initial image of the patch area is made, step 501. Power is applied to the induction coil, step 502 and, in a hand operated embodiment used as an exemplary embodiment, the inspector/operator waves the coil over the area to be inspected, step 504. The desired motion of the coil and its distance from the skin surface are dependent on the power level of the coil, RF frequency of the coil, the coil shape and size. The coil's electro-magnetic field inductively generates eddy currents in the conductive patch of LSP mesh, the skin, and the LSP mesh surrounding the patch, step 506. The coil is designed to generate currents that will tend to cross the LSP boundary when held in a chosen direction. For the embodiment shown in the drawings and employed in exemplary test embodiments of the invention, the coil is a single oblong loop which is available from Quest Integrated, Inc. with a power supply as part no. ITS 100 power supply and wand.

The eddy currents generated in the materials are of sufficient strength to generate heat in the LSP mesh, step 508. The LSP mesh will be selectively heated, depending upon local electrical paths. An IR camera is used to observe the LSP boundary areas and to image relative heating, step 510. The relative heating is determined for certain embodiments using differential thermal imaging by subtracting the initial image values created in step 501. A well-bonded LSP patch will have a uniform thermal image across the boundary of the patch area. Categorizing connectivity and resistivity in the connections between patch and substrate LSP through revealed gradients; thermal "peaks" (high resistance), thermal "plateaus" (low resistance), and thermal valleys (complete breaks/no conduction) can then be mapped for evaluation of the boundary, step 512.

To obtain the desired results in the method described, the system shown in FIG. 4 employs a focal plane array (FPA) IR camera, which is a cooled or uncooled camera in alternative embodiments. The induction current produced by the coil is used as the excitation technique, generating thermal gradients that reveal the connectivity of the mesh. The induction current heating can be generated in pulse manner in order to allow for controlled heating without damaging the mesh. In addition, the IR camera image frame can be synchronized with the current pulse so an image can be obtained before the current is applied and then captured after the current has been applied. A computer control system 28 shown in FIG. 4 provides control of both the camera and induction coil power supply as well as storage of data from the camera. Presentation of camera data, raw or processed as describe below, is provided on the monitor 30 of the computer and stored in memory for additional processing. The data values of the original unheated image are subtracted from the image under inductive heating and this difference is stored in a buffer. Additional differences can be collected and stored, for averaging purposes. This process can continue for several seconds. Once the current excitation has been turned off, the subtracted images can be integrated in order to generate a composite image. This technique, known as synchronized thermography, allows for detection of small thermal gradients and reduction of noise in IR imaging. Other image processing techniques such as Fourier filtering, edge enhancement and Laplacian filtering are applied to the final image in alternative embodiments in order to enhance the detection capability. In some cases, it may be necessary to coat the surface with a high emissivity paint in order to obtain better IR signals and reduce reflections as a portion of the surface preparation for the test.

In alternative embodiments employing an automated system, the induction coil motion is accomplished using a three axis positioning device with motion along the skin surface, coil excitation and thermal imaging controlled by the computer control system for synchronization of the data.

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. A method for verifying electrical conductivity across boundaries of lightning strike protection material comprising the steps of:

applying RF induction for generating eddy currents in LSP material proximate a joining boundary in the material;

generating heat in the LSP material due to the generated eddy currents;

providing a thermal imaging camera; and observing the LSP boundary area using the thermal imaging camera to image relative heating by
storing image frames from the thermal imaging camera;
subtracting prior stored images from subsequent stored images; and
storing resulting difference data; and,
categorizing boundary connectivity and resistivity wherein a well-bonded LSP material boundary will have a uniform thermal image, thermal "peaks" demonstrate high resistance, thermal "plateaus" demonstrate low resistance, and thermal valleys demonstrate complete breaks/no conduction.

2. A method as defined in claim 1 further comprising a preliminary step of preparing an area proximate a boundary in LSP material for thermal imaging by coating surfaces with a high emissivity paint.

3. A method as defined in claim 1 further comprising a preliminary step of erecting a shield proximate the LSP boundary for shading a surface surrounding the boundary to avoid extraneous infrared reflection from the boundary.

4. A method for verifying electrical conductivity across boundaries of lightning strike protection material in a composite material skin repair comprising the steps of:
providing a patch in a skin composite material;
bonding a LSP material patch over the composite patch;
using high power RF induction for generating eddy currents in the LSP material proximate the boundary of the LSP material patch;
generating heat in the LSP material due to the generated eddy currents;
providing a thermal imaging camera;
observing the LSP boundary area using the thermal imaging camera to image relative heating by
storing image frames from the thermal imaging camera;
subtracting prior stored images from subsequent stored images; and
storing resulting difference data; and,
categorizing boundary connectivity and resistivity wherein a well-bonded LSP material boundary will have a uniform thermal image, thermal "peaks" demonstrate high resistance, thermal "plateaus" demonstrate low resistance, and thermal valleys demonstrate complete breaks/no conduction.

5. A method for verifying electrical conductivity across boundaries of lightning strike protection material in a composite material skin repair comprising the steps of:
providing a patch in a skin composite material;
bonding a LSP material patch over the composite patch;
preparing the LSP material patch and surrounding local area for thermal imaging by coating surfaces with a high emissivity paint;
using high power RF induction for generating eddy currents in the LSP material proximate the boundary of the LSP material patch;
generating heat in the LSP material due to the generated eddy currents;
providing a thermal imaging camera;
observing the LSP boundary area using the thermal imaging camera to image relative heating;
categorizing boundary connectivity and resistivity wherein a well-bonded LSP material boundary will have a uniform thermal image, thermal "peaks" demonstrate high resistance, thermal "plateaus" demonstrate low resistance, and thermal valleys demonstrate complete breaks/no conduction.

6. A system for imaging lightning strike protection continuity in the boundaries of a composite patch comprising:
high power RF induction means for inducing eddy currents in conductive a lightning strike protection mesh proximate a periphery of a composite patch to induce thermal gradients;
an IR camera for detecting the thermal gradients; and,
means for analyzing inconsistencies in the thermal gradients including;
means for storing image frames from the IR camera;
means for subtracting prior stored images from subsequent stored images;
a buffer for storing resulting difference data.

* * * * *